United States Patent
Minoretti et al.

(10) Patent No.: US 6,322,566 B1
(45) Date of Patent: Nov. 27, 2001

(54) INTRAORAL DISTRACTOR FOR CALLUS DISTRACTION IN THE LOWER JAW

(75) Inventors: Roger Minoretti, Moehrlistrasse 63, CH-8006 Zurich; André Minoretti, Gutenswil, both of (CH)

(73) Assignees: Albino Triaca; Roger Minoretti, both of Zurich; Andre Minoretti, Gutenswil, all of (CH)

( * ) Notice: Subject to any disclaimer, the term of this patent is extended or adjusted under 35 U.S.C. 154(b) by 0 days.

(21) Appl. No.: 09/463,183

(22) PCT Filed: Jul. 17, 1998

(86) PCT No.: PCT/EP98/04421

§ 371 Date: Mar. 13, 2000

§ 102(e) Date: Mar. 13, 2000

(87) PCT Pub. No.: WO99/04715

PCT Pub. Date: Feb. 4, 1999

(30) Foreign Application Priority Data

Jul. 21, 1997 (CH) .................................. 1769/97
Jun. 30, 1998 (CH) .................................. 1383/98

(51) Int. Cl.⁷ .................................. A61B 17/58
(52) U.S. Cl. ................................................ 606/105
(58) Field of Search .................... 433/7; 606/105, 606/90, 57

(56) References Cited

U.S. PATENT DOCUMENTS

| | | | |
|---|---|---|---|
| 3,454,001 | * 7/1969 | Stockfisch | 606/105 |
| 5,364,396 | * 11/1994 | Robinson et al. | 606/105 |
| 5,540,687 | 7/1996 | Fairley et al. . | |
| 5,807,382 | * 9/1998 | Chin | 606/105 |
| 5,885,283 | * 3/1999 | Gittleman | 606/105 |
| 5,885,290 | * 3/1999 | Guerrero et al. | 433/7 |

FOREIGN PATENT DOCUMENTS

| | | |
|---|---|---|
| 29501880 | 7/1995 | (DE) . |
| 19537023 | 4/1996 | (DE) . |
| WO9714367 | 10/1996 | (WO) . |

* cited by examiner

Primary Examiner—Paul J. Hirsch
Assistant Examiner—Eduardo C. Robert
(74) Attorney, Agent, or Firm—Milde, Hoffberg & Macklin, LLP (57) ABSTRACT

Intraoral distractor for callus distraction in the human lower jaw with a proximal (posterior) and a distal (anterior) fixation part and a first displacement mechanism for a linear lengthening of the distance between the two fixation parts so as to lengthen the body of the mandible or the ramus of the mandible in the area of an osteotomy. The distractor is characterized in that the invention provides for a distraction element with a joint, the axis of articulation of which is oriented in such a way as to allow for a change in the angular position to each other of the body of the mandible and ramus of mandible in the area of the osteotomy. The one fixing part is assigned to the ramus of mandible and the other fixing part to the body of mandible. The distraction element is joined to the fixing parts in such a way that it is situated outside the tissue in the oral cavity and on the buccal side of the teeth in the vestibule.

24 Claims, 8 Drawing Sheets

INTRAORAL DISTRACTOR FOR CALLUS DISTRACTION IN THE LOWER JAW

BACKGROUND OF THE INVENTION

The invention relates to an intraoral distractor for callus distraction in the human lower jaw with a proximal (posterior) and a distal (anterior) fixation part and a first displacement mechanism for a linear lengthening of the distance between the two fixation parts so as to lengthen the body of the mandible or the ramus of the mandible in the area of an osteotomy.

Such an intraoral distractor is known from the German Patent Application DE-A1-195 37 023.

A distractor for the callus distraction in the human lower jaw is a combined surgical-orthodontical apparatus which allows the lengthening of a callus in order to correct occlusal problems, malformations, asymmetries of the mandible and miss-relations between upper and lower jaw which can be congenital or acquired, the latter for example through an accident.

Such distractors allow the linear lengthening of the mandibular ramus (ramus mandibulae) or the horizontal part of the mandible (corpus mandibulae) in the area of an osteotomy, i.e. where the bone has been cut. Furthermore, it is possible to change the angle of the mandibular angle in order to turn the occlusal plane of the lower dentition to adjust it to the occlusal plane of the upper dentition. In order to achieve this, the ramus and the corpus of the mandible are turned in the area of the osteotomy around an angle in their relation.

It is important to distinguish between intraoral and extraoral distractors for callus distraction in the human mandible. Both distractors have fixation parts which are fixated to the mandible on both sides of the required osteotomy. In the case of an extraoral distractor, fixation pins extend from these fixation elements in a percutaneous manner to the extraoral displacement units, e.g. threaded bolts or shafts and tubes. The advantage of such extraoral distractors is the good accessibility to the displacement units from outside. However, they have the disadvantage that the fixation pins are lead through the skin which results in scars depending on the size of the wound.

Intraoral distractors are placed within the oral cavity including the displacement units. Therefore, such distractors do not require the percutaneous placement of pins or fixation units. However, the space available within the oral cavity is limited which makes it difficult to optimally place the corresponding displacement units such that they are easily accessible.

The distractor, as it is known from German Patent Application DE-A1-195 37 023, comprises small fixation parts which are displaceable relative to each other. One fixation part relates to a tube, while the other relates to a threaded bolt which is guided by the tube. The threaded bolt can be turned within the tube such that, by turning, the distance between the two fixation parts can be continuously and linearly changed.

Furthermore, when installing distractors on the mandible, care must be taken not to harm the alveolar nerve (nervus alveolaris inferior) which runs within the canalis mandibulae and exits the corpus mandibulae at the foramen mentale. This nerve grants the sensibility of the lower lip and must not be harmed by fixation parts which are screwed into the mandible.

A further appliance for the fixation of bone segments, which can also be used in the area of the mandible, is known from the German Patent Application DE-A1-195 03 609. This device comprises a multi-part fixation which has single fixation units, each related to a sequence of toothed racks. The single fixation units are each anchored to the mandible by percutaneous pins. Between the two fixation units an osteotomy can be positioned. The change in position of the corresponding two bone segments is achieved by a fixation unit which is linearly moved along the toothed rack. Such a mechanism is only applicable in an extraoral form.

A further distractor is known from the U.S. Pat. No. 5,203,783. This device comprises a traction part with a housing out of which a cylindrical part similar to a piston can be moved out. At the end of the cylindrical portion, there is a disc which is fixated to the housing with a pin on the one side while it has a unit for fixation to the bone on the opposite side. By displacing—i.e., lengthening or shortening—of the piston-like cylindrical portion the disc is turned such that, with this turning, there is also an angular turn of the fixation part fixed to the bone. This device is quite large and therefore not usable as a distractor for callus distraction in the mandible, especially not in an intraoral form of a distractor.

SUMMARY OF THE INVENTION

Based on the existing state of the art, it is a principal object of the present invention to improve an intraoral distractor for callus distraction in the mandible as described above in a way that it allows—although intraoral—not only a linear distraction of the corpus mandibulae or ramus mandibulae in the area of an osteotomy but also a change of the angle between these two portions of the mandible and offers also the possibility of lengthening of corpus and/or ramus mandibulae.

This object is achieved by a distractor with above mentioned characteristics according to the invention by the characterizing part of claim 1 in that a distraction element comprising a joint, wherein the axis is oriented such that a change of the angle relation between corpus mandibulae and ramus mandibulae becomes possible in the area of the osteotomy wherein one fixation part is connected to the ramus mandibulae while the other is connected to the corpus mandibulae and whereby the distraction element is connected to the fixation parts such that it lies outside of the tissues in the oral cavity, buccaly of the dentition in the vestibulum. This distractor for application in the mandible allows the lengthening of the ramus mandibulae as well as the horizontal part of the mandible (corpus mandibulae) by callus distraction single or in combination and in addition, which is decisive, it allows based on its joint the change of the mandibular angle. By such a change in the mandibular angle, the occlusal plane of the lower dentition can be turned and adapted to the occlusal plane of the upper dentition. In order to do so, the osteotomy is preferably positioned through the angulus mandibulae about bisecting the angle. In the area of this osteotomy it is then possible to lengthen the ramus and/or corpus mandibulae and at the same time to change the angulation of the distractor in the joint therefore adapting the angle between corpus and ramus mandibulae to the occlusal plane and the occlusion in the upper jaw. A further important feature is the positioning of the distraction element outside of the tissues within the oral cavity, buccaly to the dentition in the vestibulum. This allows the intraoral application of the distractor even though it has a joint and the mechanisms to lengthen the horizontal and vertical branches of the mandible. Furthermore, such an appliance is usable for the right as well as the left side of the mandible. It can be applied in a mirror symmetry of the distractors to each other and each side of the mandible manipulated independently. The application of such appliances on both sides or only one side of the mandible depends on the type of mandibular misspositioning.

The distractor is fixated with screws proximal (posterior) of the osteotomy on the ramus mandibulae, independently of the required corrective movement; the fixation distal (anterior) of the osteotomy is done in a first variation with screws in the chin area, apically of the ipsilateral front dentition, or, in a second variation, distal (anterior) to the osteotomy with screws on the corpus mandibulae, posterior to the foramen mentale.

With the above described embodiment, the required osteotomy is done from enoral in the mandibular angle (angulus mandibulae) with absolute preservation of the inferior alveolar nerve, by doing a corticotomy buccaly and lingually and fracturing the cancellous bone manually. By the help of an extraoral, transbuccal approach in the form of a stab incision of the skin, the lower edge of the mandible is corticotomized in the area of the mandibular angle with a bone cutter and with a drill the wholes are drilled for the screws in the ramus ascendens (ramus mandibulae). The screws are inserted transbuccally as well.

In the above mentioned first variation, the approach in the chin area is taken from enoral by a cut in the mobile muccosa in the vestibulum in a distance of about 8 mm to the border of the attached gingiva of the mandibular front in the area of the canine. The exit of the nervus mentalis at the foramen mentale is exposed. In the second variation, the incision is taken from enoral in the buccal vestibulum in the mobile muccosa; the periost is partially detached from the corpus mandibulae, the nervus mentalis at the foramen mentale exhibited and the distal (anterior) branch, which is preferably vertical in such a variation and reaches down to the inferior edge of the mandibula, fixed with screws posterior to the foramen mentale. The proximal (posterior) to the bone fixed branch exits at the anterior edge of the ramus mandibulae through the mucosa into the buccal vestibulum. He distal (anterior) branch exits into the buccal vestibulum in the mucco-gingival fold of the mandibular front in the first variation and in the second variation through the mucco-gingival fold of the buccal vestibulum into the oral cavity.

The central unit of the distractor is the distraction element with the integrated joint. The distraction element is positioned outside of the soft tissues buccaly of the dentition in the vestibulum of the oral cavity. Preferably, also the first displacement traction is made part of this distraction element. Furthermore, the distraction element of the intraoral distractor is held detachable in the area of interfaces between the local disconnection areas. This construction allows the removal of the distraction element, in order to adapt it through a modified variation to the situation in the mandible during the treatment of the patient, if necessary; furthermore it becomes possible during the surgical intervention, to first position the fixation elements and to sew the wounds before the distraction element is connected to the fixation parts.

In many cases a linear displacement, as mentioned above, is sufficient to linearly change the distance between the two fixation parts. However, in special cases when besides of the corpus mandibulae also the ramus mandibulae requires lengthening it can be advantageous to include a second linear displacement traction which allows a linear change of the distance between the two fixation parts in a direction orthogonal to the linear displacement direction of the first traction. With this double linear displacement possibility in addition to the angular turning joint, virtually every adaptation in space of the mandibular occlusal plane to the occlusal plane of the maxillary dentition becomes possible. In such an arrangement in a preferable embodiment of the distractor, the second displacement traction should be arranged with the distraction element such that all displacement possibilities can be activated centrally on the distraction element and therefore well accessible in the oral cavity.

The sequence of the arrangement of the single displacement or angulation tractions within the distraction elements may be changed if required.

If a first and a second displacement traction are required, they should preferably be arranged such that the first displacement traction mainly lengthens the corpus mandibulae while the second displacement traction mainly lengthens the ramus mandibulae.

In order to create simple construction for the linear displacement tractions, an embodiment of the distractor includes a distraction element with a branch which is connected to the fixation part screwed onto the ramus mandibulae and a branch which is connected to the fixation part on the corpus mandibulae. Furthermore, in such an arrangement both branches with their free ends may overlap seen in the direction of the axis of the corpus mandibulae, such that over the free frontal end of the overlapping part pointing towards the frontal dentition a corresponding displacement possibility can be included, for example a threaded bolt.

If the distractor is constructed with a first and a second displacement traction, the first displacement traction should be connected to that branch of the distraction element which is related to the fixation part connected to the corpus mandibulae, while the second displacement traction lengthens the ramus mandibulae.

A simple space conserving displacement possibility is possible by splitting the branch making part of the fixation part on the corpus mandibulae into two parts and by linearly displacing the two parts of the branch relative to each other by the help of an integrated threaded shaft. Such a threaded rotating shaft is again well accessible from the side of the frontal dentition.

Furthermore, the fixation part related to the ramus mandibulae should be constructed or formed such that it can be fixated on the buccal respectively lateral side of the ramus mandibulae.

Because the transversal distance between the mandibular condyles should not be changed during the distraction, the axis/axes of the linear distraction traction(s) should be arranged parallel to the sagittal plane and the axis of the angulation joint should be arranged orthogonal to the sagittal plane. This orthogonal position is important also with respect to the axial orientation of the mandibular condyles.

In order to achieve a compact construction, leaving the possibility of a fine tuning, the first and/or the second displacement traction should be formed by a toothed rack and an engaging worm wheel. With such an arrangement it becomes possible to turn the worm wheel from the frontal side while the displacement of the tooth rack is possible in an orthogonal direction. This means that with such a construction utilizing a worm wheel it is possible to achieve a displacement around a specific angle between the two direction of the displacement tractions.

A further constructive arrangement for the change of the angular relation between ramus mandibulae and corpus mandibulae is possible by utilizing a gear segment with helical gearing and a connected worm wheel; this brings the same advantages as described above. When utilizing such a worm wheel the gear segment should be attached on the fixation part connected to the ramus mandibulae, while the worm wheel is connected to the fixation part relating to the corpus mandibulae.

In combination with a distraction element which is held between the fixation parts, solvable in the area of interface portions, as described further above, the interfaces between the distraction element and the corresponding fixation unit should each be constructed with a linear guidance. Thereby the guidance direction is parallel to the sagittal plane and about orthogonal to the occlusal plane of the mandible. Here a simple constructive arrangement can be found by building the linear guidance at the interface to the corpus mandibulae in the form of a butt strap reaching into a nut guidance. As alternative to this, a simple constructive arrangement is also possible is also possible by constructing the linear guidance at the interface to the ramus mandibulae in the form of a rod with a tube or claw gliding over it. The connection between the rod guidance with circular cross section and the tube or claw gliding over it should furthermore be constructed such that the distraction element can be arranged parallel to the sagittal plane by turning it around the axis of the rod guidance. Furthermore, such an arrangement makes it possible that the tube is adjustable along the guidance rod in direction of its axis in order to achieve an adaptation in height. Thereby an adjustment possibility should be included which allows a fixation of the tube on the rod guidance in a desired position. Such a rod guidance should make part of the fixation unit.

Further details and characteristics of the present invention are found in the following description of constructive examples on the basis of the corresponding drawings.

BRIEF DESCRIPTION OF THE DRAWINGS

FIG. 10B shows a view of the part in FIG. 10A from the direction of visual vector XB in FIG. 10A; and FIG. 10C shows a view on the part from the direction of visual vector IX in FIG. 10A.

DESCRIPTION OF THE PREFERRED EMBODIMENT

The preferred embodiments of the present invention will now be described with reference to FIGS. 1–10 of the drawings. Identical elements in the various figures are designated with the same reference numerals.

Figure 1:
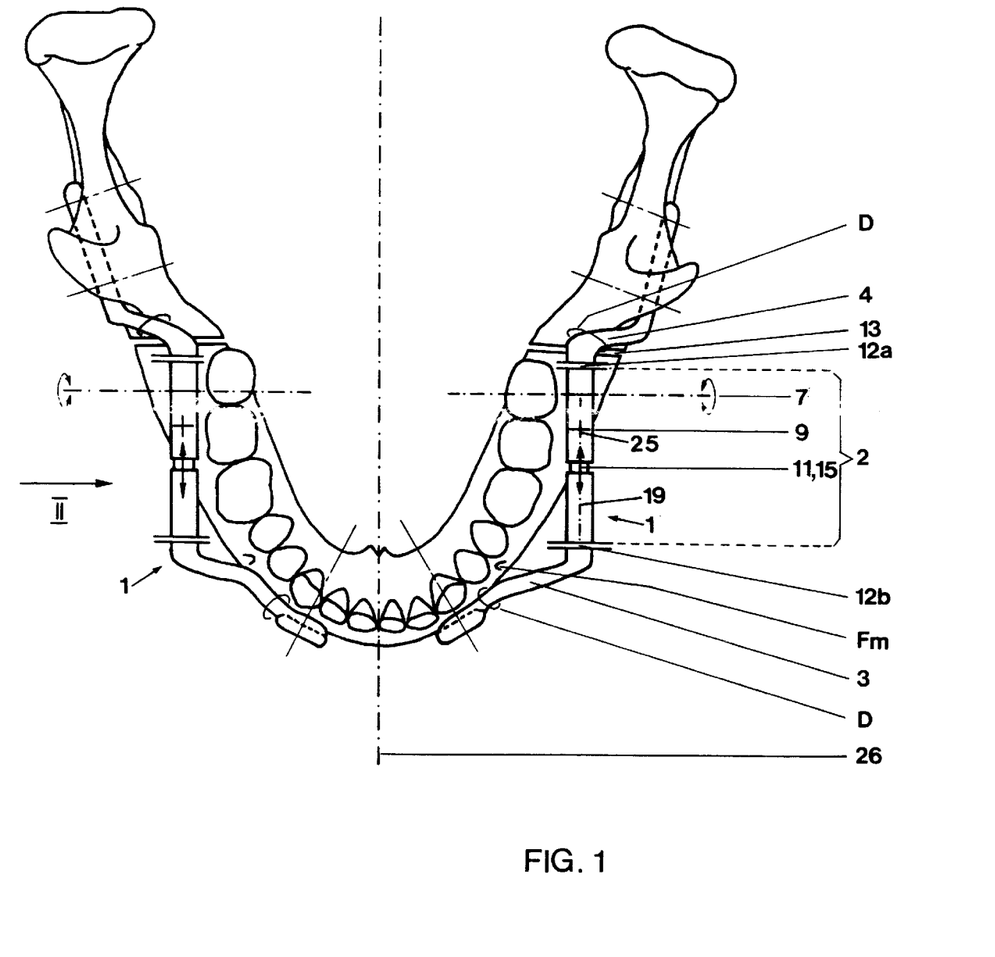
FIG. 1 shows a top view of a mandible with two intraoral distractors constructed in mirror symmetry to each other, according to a first embodiment.
Figure 2:
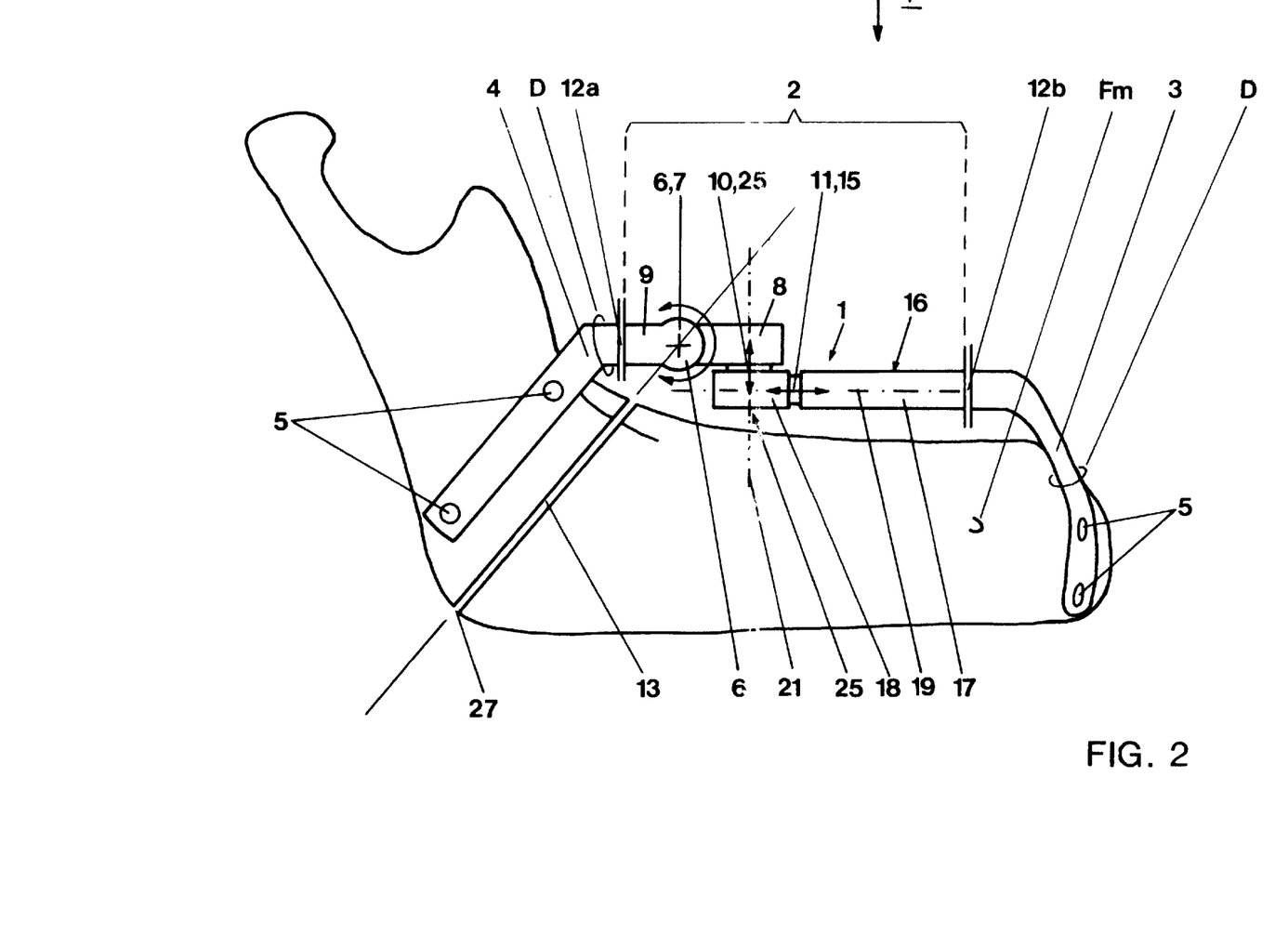
FIG. 2 shows a side view of the distractor according to FIG. 1 in direction of the visual vector II in FIG. 1.

The distractor 1 comprises in a first embodiment as shown in FIGS. 1 and 2 a distraction element 2 between the two fixation units 3 and 4. The fixation element 3, i.e. the distal (anterior) branch emerges in the muco-buccal fold of the vestibulum of the mandibular front into the oral cavity. The other fixation unit 4 emerges through the mucosa at the anterior edge of the ramus mandibulae into the buccal vestibulum on the position marked with D. The corresponding fixation units 3, 4 are adapted to the curvature of the corpus mandibulae and the ramus mandibulae, respectively, and include each two, possibly three or four fixation wholes 5, as seen in the side view of FIG. 2.

A central part of the distraction element 2 is a joint 6 the axis of which is marked with the sign 7. On both sides of the joint 6 two branches 8, 9 are emerging, whereby branch 8 of the distraction element 2 is connected to the fixation unit 3, while branch 9 is connected to the fixation unit 4. The distraction element 2 is located, as seen in FIG. 2, outside of the tissues in the buccal vestibulum lateral of the dentition and enables a distraction in cranio-caudal direction as indicated by the double-arrow 10, and a displacement in posterior-anterior direction, as indicated by double-arrow 11. Furthermore, the transitional area between the fixation parts 3 and 4 and the distraction element 2 respectively its branches 8 and 9 include interfaces 12a and 12b; at these interfaces 12a and 12b the distraction element 2 can be disconnected from the proximal (posterior) fixation part 4 and the anterior fixation part 3 respectively reconnected. This eases the sewing of the mucosa in the vestibulum during the surgery and also enables the exchange of the distraction mechanism during the treatment if this should be required by the treatment.

In the case of very long distraction distances it could be possible that the distance available within the distraction element has been used up, although a further distraction would be required clinically. In such a case the distraction element 2 could be exchanged against another one which enables a larger distraction distance. Furthermore the removal of the distraction element 2 allows that when the distraction goal is reached the distraction distance respectively the angle change achieved by the joint 6 can be measured and for the retention phase, i.e. until the final healing, a corresponding place holder with the required dimensions can be installed instead of the distraction element 2. Such a place holder can be dimensioned very small such that the replacement of the distraction element 2 by such a place holder can improve the comfort of wearing it for the patient.

As can be seen in FIG. 2, the joint 6 with its axis 7 is positioned in the line of the osteotomy 13 respectively in the plane of the osteotomy, whereby the osteotomy is preferably located in the angulus mandibulae 27, bisecting the angle. Because of the position of joint 6 in the plane of the osteotomy 13, the change of the angle between the branches 8 and 9 relative to each other in direction of the double arrow 14 allows an even change of the angle between ramus mandibulae and corpus mandibulae. An additional correction may take place simultaneously to the change in the angle, or in additional steps, by a linear lengthening or shortening of the branch 8 connected to the corpus mandibulae in direction of double arrow 11, or by a displacement orthogonal to the occlusal plane respectively orthogonal to the displacement direction indicated by double arrow 10.

For such a lengthening or shortening in direction of double arrow 11, a first displacement traction 15 is proposed;

within this traction, the free branch 16 of the distal (anterior) fixation part 3, which is in its length direction about parallel to the occlusal plane, is divided into two segments 17 and 18 which are connected with rotational securing by a threaded rod with an axis indicated by line 19. The threaded rod 19 is guided until the anterior end 20 of segment 17 and is accessible for a tool at this position with a not more precisely defined opening. The frontal side of the threaded bolt may exhibit a slot, a cross recession an hexagon socket or a pin such that a corresponding tool may be engaged. With such a tool the threaded rod may be turned to change the distance between segments 18 and 19 in the area of double arrow 11, in order to move the corpus mandibulae in the area of the osteotomy relative to the ramus mandibulae in the direction of double arrow 11.

In order to displace the corpus mandibulae in direction of double arrow 10, i.e. in cranio-caudal direction (or about orthogonal to the occlusal plane), the segment 18 of the branch 16 of the anterior fixation part 3 is positioned below branch 8 of the distraction element 2. In this direction branch 8 and segment 18 are connected by a further threaded rod of which the axis is indicated by line 21. In this way a second displacement traction 25 is formed. By turning the threaded rod with a corresponding tool at its frontal end (for instance by a connection in form of a conical gear wheel the threaded rod may be easily adjusted in direction of double arrow 10, accessing it from the oral cavity.

As shown in the first variation of the intraoral distractor, shown in FIGS. 1 and 2, it is despite of a simple mechanical construction possible to achieve a change in the orientation of ramus mandibulae and corpus mandibulae relative to each other with three degrees of freedom, i.e. in direction of double arrows 10 and 11 as well as around the joint axis 7; therefore the occlusal plane of the mandible can be exactly adjusted to the occlusal plane of the maxilla. The construction of the distractor with the threaded rods is very compact and of little size, such that the patient is hindered only to an extent which is absolutely necessary. Furthermore, this distractor has no parts sticking out which could lead to injuries within the oral cavity; this is true also when the displacement traction have been activated and the corresponding parts 8, 18 and 18 displaced relative to each other in distance.

Because of the arrangement of the anterior fixation part 3 in the area of the chin as shown in variation 1 of the distractor shown in FIGS. 1 and 2, the access to fixate this fixation part 3 can be achieved by a dissection from enoral in the mobile mucosa of the vestibulum, in a distance of about 8 mm from the border to the attached gingiva in the mandibular front. In the figures, the place where the mucosa is penetrated is marked with D. Furthermore, it is obvious that because of the arrangement of fixation part 3 in this area of the chin, the foramen mentale FM and therefore the canalis mandibulae and the nervus alveolaris running through it are not endangered.

While FIGS. 1 and 2 are depicting the right-sided distractor 1, it is obvious that the left-sided distractor 1 is of a corresponding but mirror symmetric construction. The left-sided distractor 1 and the right-sided distractor 1 may therefore be activated independent from each other in the two linear directions as well as around the joint axis 7, if a bilateral correction of the mandible is necessary.

The embodiments described in the subsequent FIGS. 3 to 10 are comparable with above embodiment as described in FIGS. 1 and 2, with respect to the possibilities of adjustment in direction of double arrows 10 and 11 as well as around the joint axis 7.

Therefore, the components in the following embodiments, as long as they are comparable with those of embodiment 1, are bearing the same markings such that above description with respect to FIGS. 1 and 2 can analogously be transferred to the following figures with respect to such comparable parts and their function.

Figure 3:
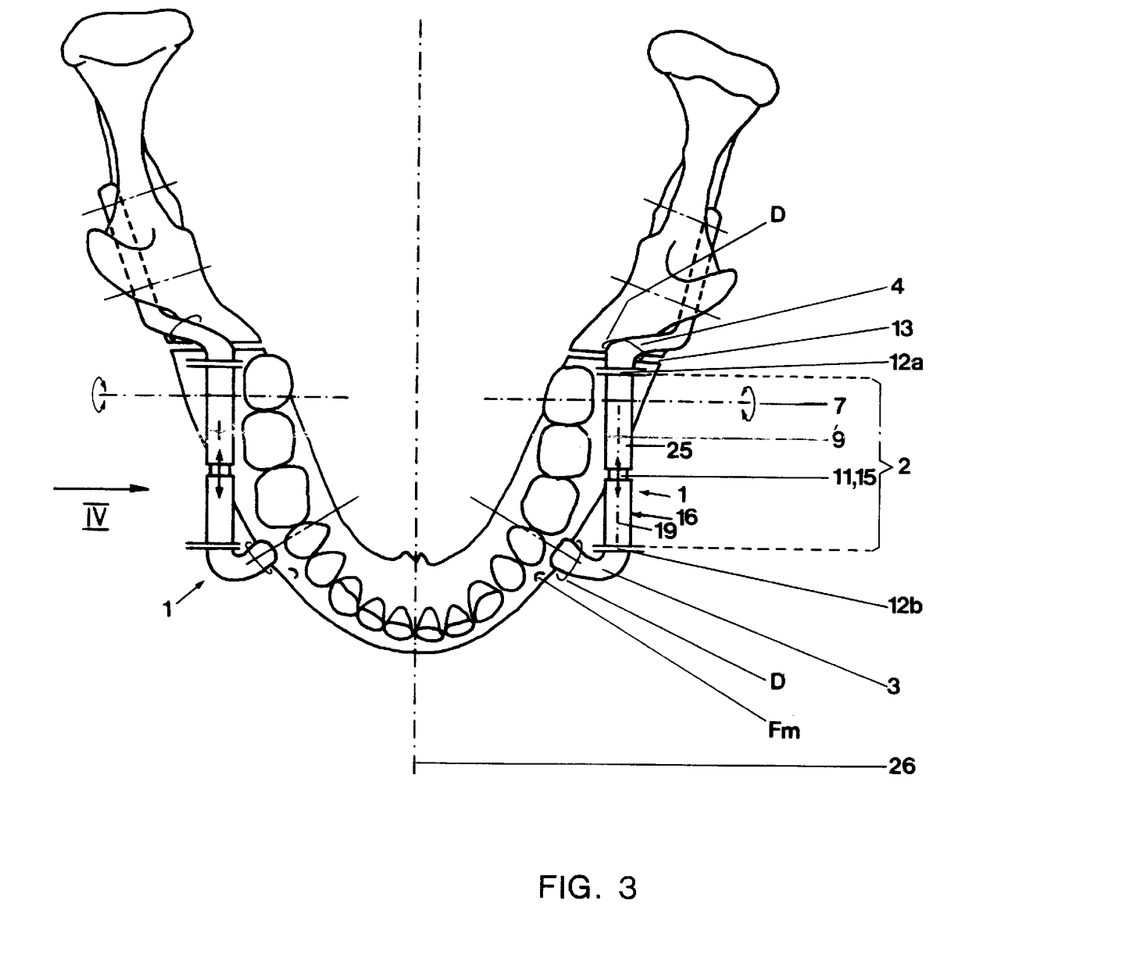
FIG. 3 shows a second embodiment of an intraoral distractor in a top view.
Figure 4:
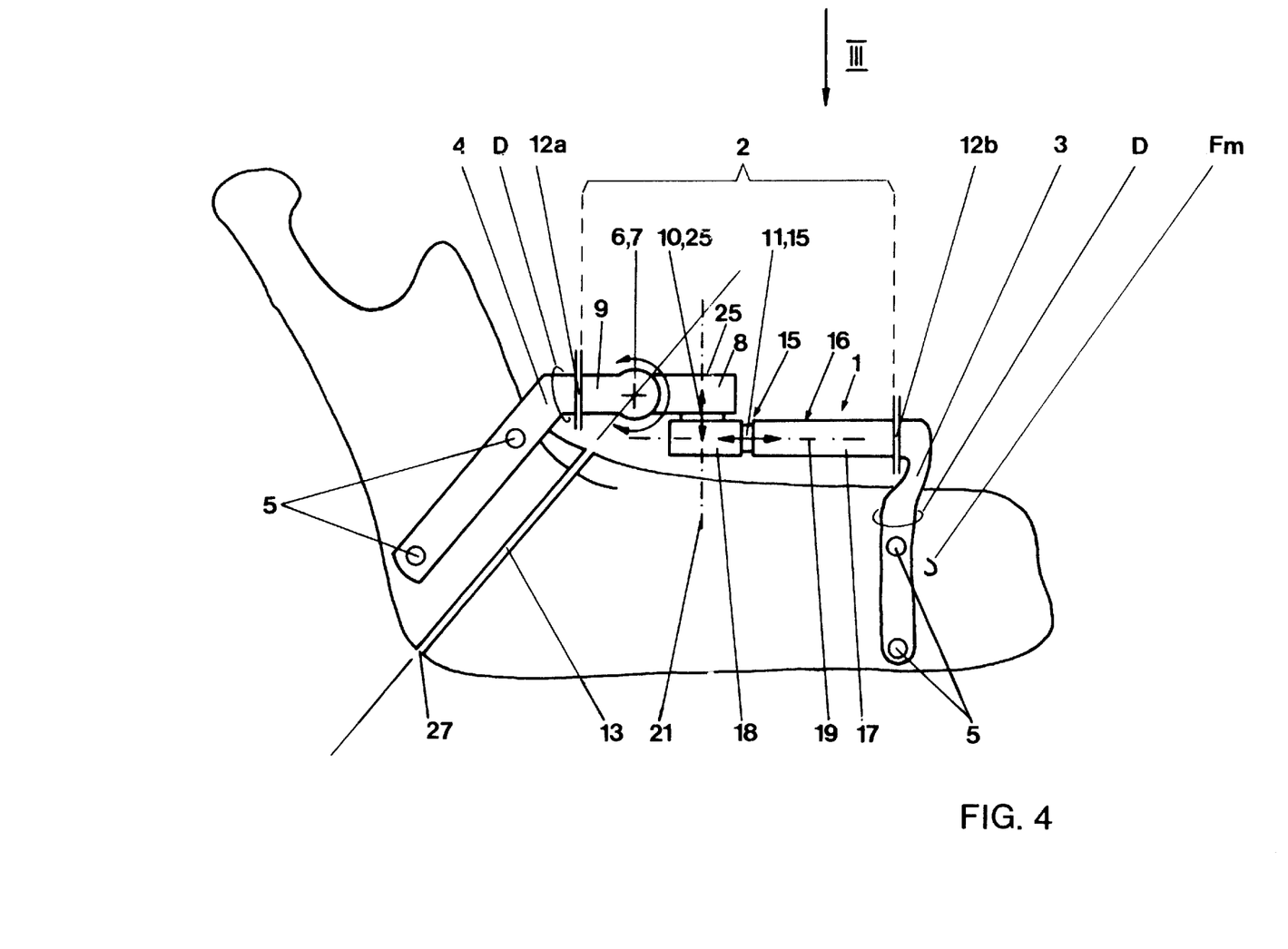
FIG. 4 shows a side view of the distractor according to FIG. 3 in direction of the visual vector IV in FIG. 3.

In the second embodiment, as shown in FIGS. 3 and 4, the distraction element 2 of the distractor is corresponding to the construction of the first embodiment. The same is true for the posterior fixation part 4 which is connected to the ramus mandibulae. On the other side, the anterior fixation element 3 which is related to the corpus mandibulae is different in that its fixation portion is not fixated to the chin but to the osteotomy side of the foramen mentale, i.e. posterior to Fm. With this distractor the incision is taken from enoral in the buccal vestibulum of the mobile mucosa; the periost is elevated partially at the corpus mandibulae and the nervus mentalis exhibited at the foramen mentale Fm; the anterior fixation part 3 which is here about orthogonal to the segment 17 of the free branch 16 and reaches to the lower edge of the mandible is fixated with screws through the holes 5 (posterior to the foramen mentale).

The holes 5 are positioned far apart such that a sufficient space is remaining between the holes 5 in order not to harm the nervus alveolaris inferior during the surgery. This second embodiment represents a possible alternative compared to the first embodiment. However, it usually requires a second skin incision in order to insert the screws from trans-buccal; therefore the surgical approach may be more complicated. Furthermore, usually only the caudal fixation screw may be inserted bicortically, while the cranial screws of fixation part 3 may usually only be anchored monocortically because of the dental roots. On the other hand this embodiment has the advantage that the forces can be transferred to the distraction of the osteotomy with a shorter lever arm, since the fixation unit 3 is closer to the osteotomy 13.

The third embodiment of an intraoral distractor according to the present invention, as it is shown in FIGS. 5 and 6, again corresponds to the first and second embodiment with respect to the distraction element 2 and the posterior fixation unit 4 (FIGS. 1–4). In contrast to the first and second embodiment, the anterior fixation unit 3 is constructed from four segments. These are segment 17 (comparable to segment 17 of the first and second embodiment), a further segment 22 running parallel to it which reaches out in direction of the osteotomy 13, an oblique interpositioned segment 23 and the fixation segment 24 with integrated holes 5. This fixation segment 24 runs along the lower edge of the corpus mandibulae and reaches out almost to the osteotomy 13. As can be seen in the side view of FIG. 6, this arrangement leaves the area of the chin and the area of the mandible posterior to the foramen mentale free.

Figure 5:
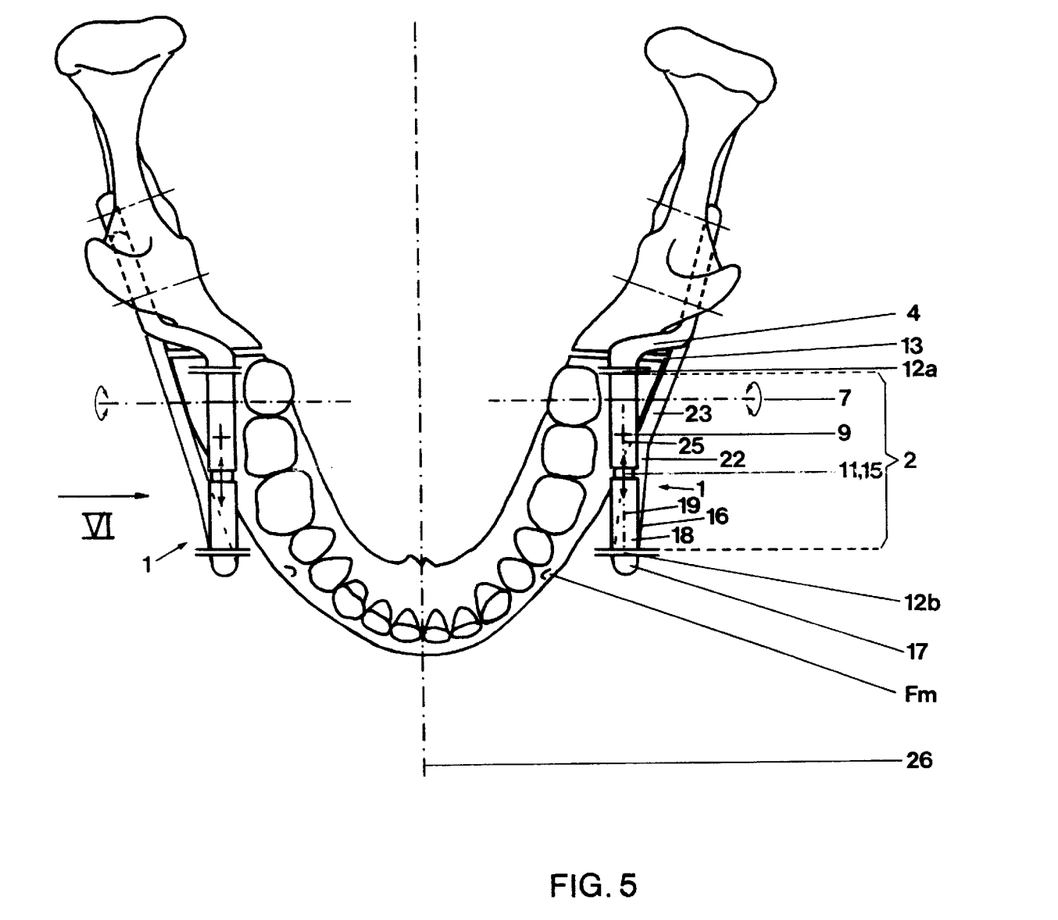
FIG. 5 shows a third embodiment of an intraoral distractor in a top view.
Figure 6:
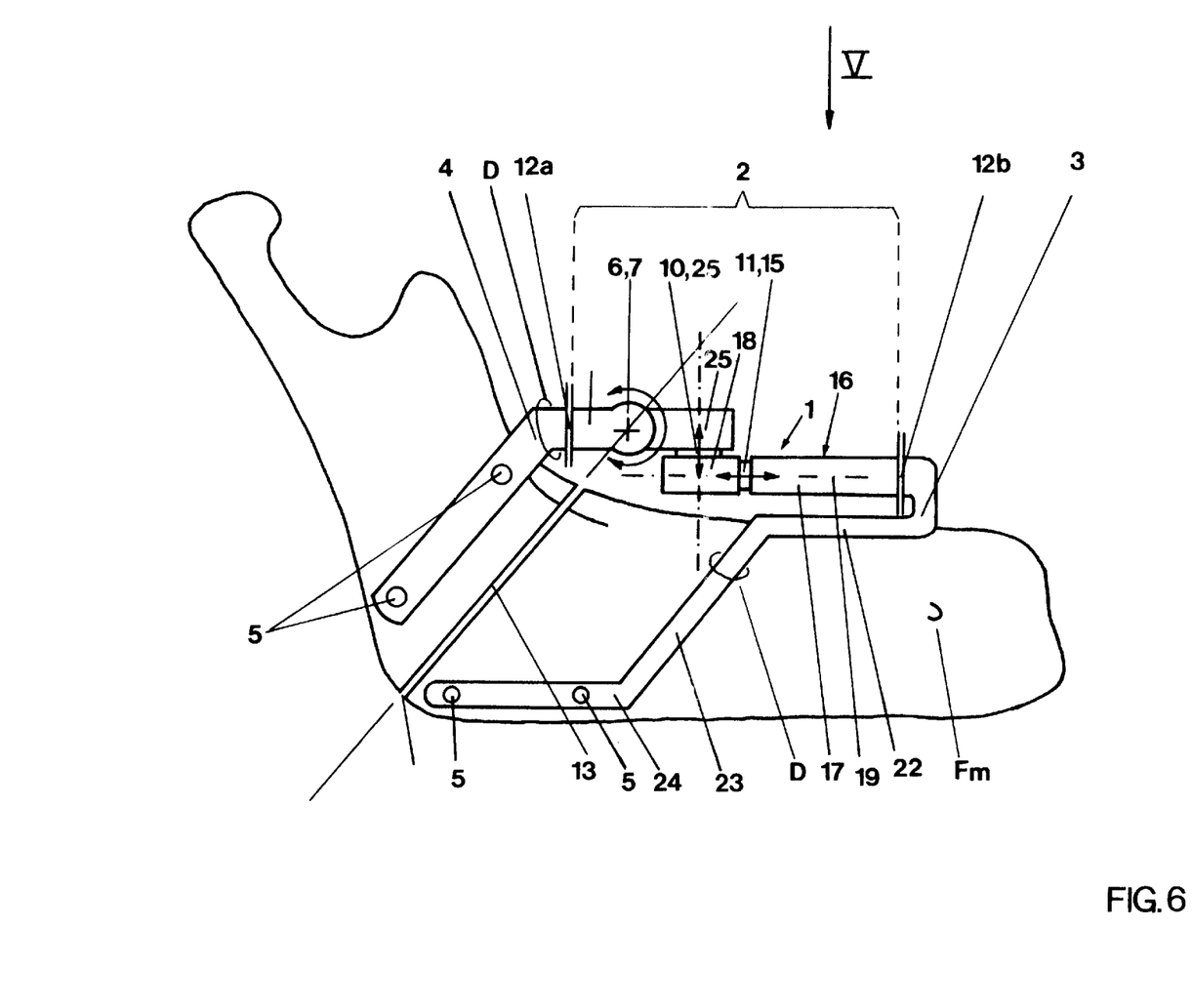
FIG. 6 shows a side view of the distractor according to FIG. 5 in direction of the visual vector VI in FIG. 5.

This arrangement has the advantage that the distraction forces are acting directly on the osteotomy without long leverage distances; this could be an advantage compared to the first embodiment for distractions in cranio-caudal direction 10. Usually, the same trans-buccal access which is required for inserting the screws of the posterior fixation unit 4 can also be used to insert the fixation screws of segment 24 of the fixation unit 3. The screws can usually be inserted bicortically since the nervus alveolaris inferior and the dental roots are located cranially from this area. However, with this design, the periost in the area of the osteotomy has to be more elevated for the fixation unit 3.

Figure 7:
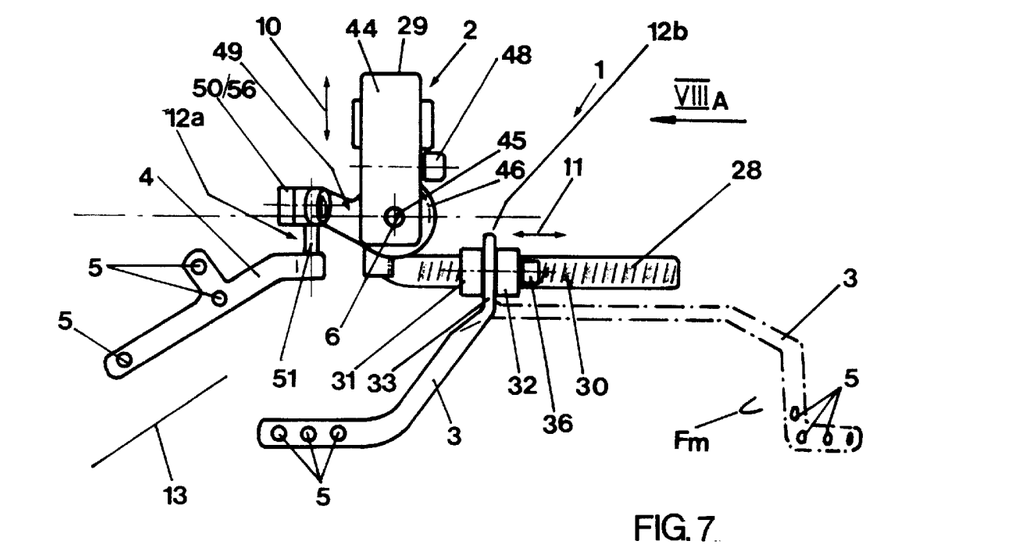
FIG. 7 shows a scheme of a fourth embodiment of a distractor with a worm wheel drive.
Figure 8:
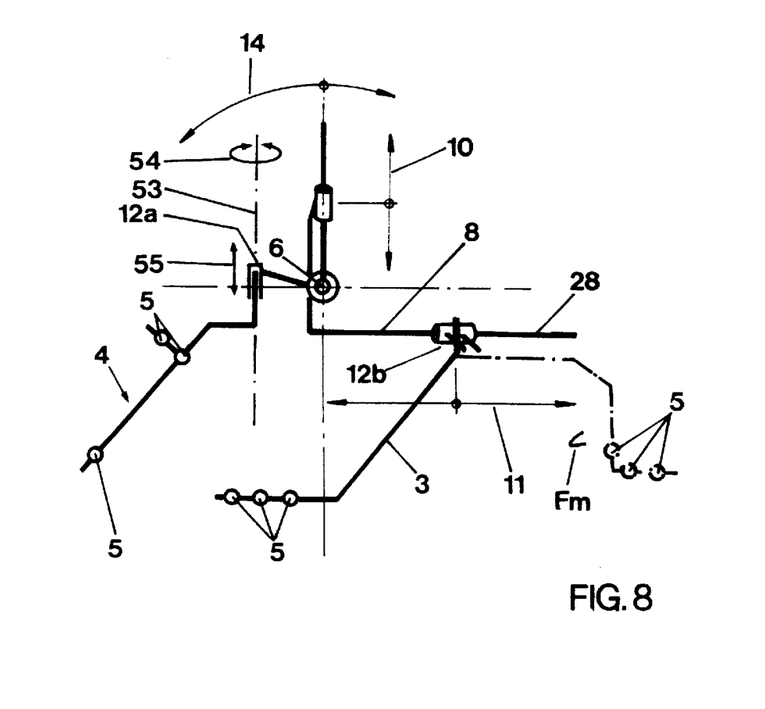
FIG. 8 shows a depiction of the lines of action and the fixation points of the distractor in FIG. 7.

It should be noted that the distraction element 2 is running parallel to the sagittal plane 26 with respect to branches 8, 9 and the free branch 16 of the fixation unit 3 with the segments 17 and 18. Also, the joint axis 7 of the angulation device is orthogonal to the sagittal plane. In FIGS. 7–10 a further, fourth embodiment of a distractor 1 is shown. The single parts are not drawn fixated to the mandible in order to better illustrate the technical details. Also this distractor 1 is, as shown in FIGS. 7 and 8, a distractor which allows with respect to three degrees of freedom a modification of the mandibular angle in the area of the osteotomy 13, i.e. of the angel between corpus mandibulae and ramus mandibulae. On the one hand, again a joint 6 is integrated, on the other hand, a linear displacability in the posterio-anterior direction, indicated by double arrow 11 and a desplacability in the cranio-caudal direction, indicated by double arrow 10 is possible.

The single lines of action of distractor 1 in FIG. 7 are again schematically shown in FIG. 8 in order to give a better overview.

The distractor 1 of the fourth embodiment has again an anterior fixation unit 3 with fixation holes 5. Thereby the fixation unit with full lines corresponds to an arrangement as it has been described in the third embodiment and is shown in FIGS. 5 and 6 (see especially FIG. 6), while the fixation unit 3 drawn with a dotted line is corresponding to an arrangement like in the first embodiment (see FIGS. 1 and 2). The posterior fixation unit 4 is in its arrangement comparable with the above described embodiments. However, in this posterior fixation unit 4 of FIG. 7 are three fixation holes 5 integrated, which are arranged in an L-shape allowing a better dispersion of the forces acting upon this fixation points, as compared to a purely linear arrangement of the holes. The same is true also for the shown arrangement of the fixation holes 5 of the distal (anterior) fixation unit 3, which are also arranged in an L-shape in the design variation of FIG. 7.

Figure 9A:
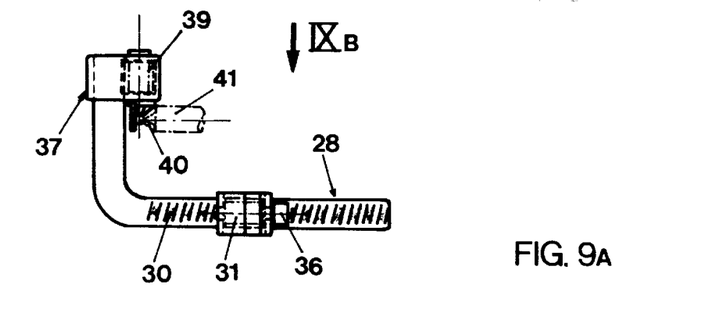
FIG. 9A shows a side view of the anterior part of the distractor element in FIG. 7.
Figure 9B:
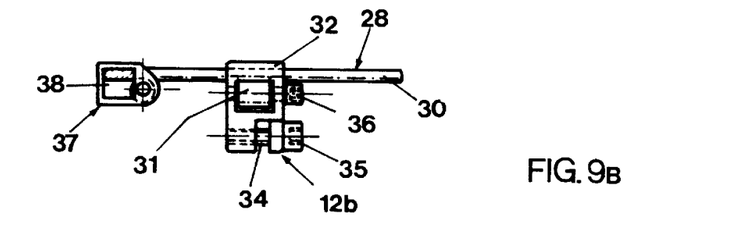
FIG. 9B shows a view on the part of FIG. 9A seen from the direction of the visual vector IXB in FIG. 9A.
Figure 10A:
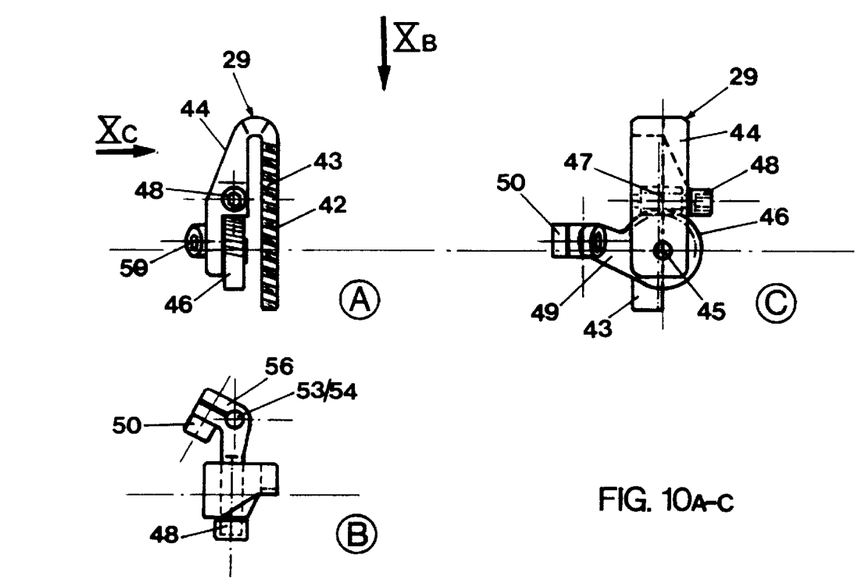
FIG. 10A shows a view of the joint portion of the distraction element of FIG. 7 seen from the direction of the visual vector IIIA.

The distraction element 2 is composed of two important components, one of which is a flat, L-shaped bow 28, which is shown in more detail and two different views in FIGS. 9A and 9B. Thereby this bow is comparable to the branch 8 of the distraction element as drawn in FIG. 2. The second important component is a U-shaped bow 29, comparable to branch 9 in the design variation according to FIG. 2.

The L-shaped bow 28 is constructed as flat component in the form of a stripe with a helical gearing 30 on the buccal side. This helical gearing is engaged by a worm gear 31 which is held in a housing part 32 which again is held solvable in a clamping component 34 at a vertical end 33 of fixation unit 3; this clamping component 34 forms at the same time an interface 12b, in order to release the distraction element 2 from the fixation unit 3. To release it, the corresponding clamping screw 35 is loosened, such that the L-shaped bow 28 can be removed in upward direction from the vertical end 33. The worm gear 31 has a rotational axis which is parallel to the plane of the helical gearing 30, it is accessible from the frontal side by the help of a tool head 36, for instance constructed with an inner hexagon socket. In this way, the worm gear 31 can be linearly displaced along the long branch of the L-shaped bow, i.e. along its helical gearing 30. On the short, vertically upward pointing branch of bow 28 there is a connection part fixated with a slot 38 as well as a worm gear 39 oriented parallel to this branch with its driving axle. This worm gear 39 bears a bevel gear 40 at is lower end which allows its rotational activation with a corresponding tool 41 as indicated in FIG. 9A. Because of this arrangement, the worm gear can be activated from anterior through the oral cavity as well.

In the slot 38 one of the branches of the U-shaped bow 29 (see FIG. 10A) is inserted, such that its lateral helical gearing 43 is engaged by worm gear 39. By turning the worm gear 39, the L-shaped bow can be displaced up and down in direction of double arrow 10 (FIGS. 7 and 8). The other branch 44 of the U-shaped bow bears the axis 45 of a spur-gear with helically formed teeth, where this spur-gear with helically formed teeth is engaging a further worm gear 47 of which again the axis is oriented such that it can be rotated from frontal with a tool head 48. By turning this tool head 48, the spur-gear 46 with helically formed teeth is turned around its axis 45, such that a lever arm 49 is rotated which is connected to it and reaching out towards posterior (see FIG. 7). This lever arm 49 can be clamped to a rod 51, which is located at the free end of fixation unit 4, by a clamping tube 56 with a clamping screw 50. This way a second interface 12A is formed. As can be seen, the distraction element 2, as shown with its details in FIGS. 9 and 10, can be loosened any time from the fixation units 3 and 4 by loosening the posterior interface 12A between clamping screw 50 and rod 51 and by loosening the anterior clamping connection in the area of clamping unit 34 and clamping screw 35. Therefore distraction element 2 can be exchanged for instance to revise it or to adjust it to the changed conditions during treatment. Furthermore, the rod guidance 51 and the clamping tube 56 engaged to it allow a displacement in direction of double arrow 55, i.e. the tube can be modified in its height position along the rod guidance 51 and fixated. Furthermore, a rotation about the axis created by the rod guidance 51 becomes possible in direction of double arrow 54 (see FIG. 8) to allow a further adjustment according to the given situation. Furthermore, this distractor 1 has the advantage that all adjustments can be done from the front since all activation units are well accessible with tools from the front.

It must be noted that FIG. 8 is about correct in scale, such that the situation with respect to lever arms and points of engagement and connection can be taken from this figure with sufficient precision.

There has thus been shown and described a novel intraoral distractor for callus distraction in the lower jaw which fulfills all the objects and advantages sought therefor. Many changes, modifications, variations and other uses and applications of the subject invention will, however, become apparent to those skilled in the art after considering this specification and the accompanying drawing which discloses the preferred embodiment thereof. All such changes, modifications, variations and other uses and applications which do not depart from the spirit and scope of the invention are deemed to be covered by the invention, which is to be limited only by the claims which follow.

What is claimed is:

1. In an intraoral distractor for callus distraction in a human mandible with a proximal (posterior) and a distal (anterior) fixation unit and with a first displacement traction for a linear modification of distance between the proximal and distal fixation units, in order to lengthen a corpus mandibulae or a ramus mandibulae in an area of osteotomy, the improvement comprising a distraction element with a joint of which a joint axis is oriented such that it allows a modification of an angle between corpus mandibulae and ramus mandibulae relative to each other in the area of the osteotomy, wherein a first fixation unit is adapted to be attached to the ramus mandibulae, while a second fixation unit is adapted to be attached to the corpus mandibulae, wherein the distraction element is connected to the first and second fixation units in such a way that, when the fixation units are attached to the ramus and corpus mandibulae, respectively, the distraction element is positioned outside of tissues within an oral cavity and buccal to dentition in a vestibulum; and wherein said distraction element is held between said first and second fixation units in a way that it can be loosened and removed by means of interfaces.

2. Intraoral distractor of claim 1, wherein said first displacement traction is part of said distraction element.

3. Intraoral distractor according to claim 1, wherein a second, linear displacement traction is provided in order to enable a linear change of the distance between said fixation units in a direction with a component orthogonal to linear displacement achieved with said first displacement traction.

4. Intraoral distractor according to claim 3, wherein at least one of the first and second displacement traction are formed by a toothed rack and an engaging worm gear.

5. Intraoral distractor according to claim 3, wherein said second displacement traction is part of said distraction element.

6. Intraoral distractor according to claim 3, wherein said first displacement traction lengthens the corpus mandibulae and said second displacement traction lengthens the ramus mandibulae.

7. Intraoral distractor according to claim 1, wherein said distraction element has a first branch, which is related to said first fixation unit and a second branch which is related to said second fixation unit.

8. Intraoral distractor according to claim 7, wherein the two branches have two ends which overlap in a direction of a longitudinal axis of the corpus mandibulae.

9. Intraoral distractor according to claim 8, wherein said two ends form a part of a second displacement traction such that the two ends can be modified in their distance to each other.

10. Intraoral distractor according to claim 9, wherein said second displacement traction includes a threaded rod for changing said distance.

11. Intraoral distractor according to claim 7, wherein the first displacement traction lengthening the corpus mandibulae is related to the second branch which comprises part of the second fixation unit.

12. Intraoral distractor according to claim 11, wherein the second branch is segmented into two segments which are adjustably connected by a threaded rod guided within it.

13. Intraoral distractor according to claim 12, wherein the threaded rod is accessible via an end of the second branch which comprises part of the second fixation unit, in order to adjust it.

14. Intraoral distractor according to claim 1, wherein the joint is part of the first fixation unit.

15. Intraoral distractor according to claim 1, wherein the first fixation unit is adapted to be fixated on the buccal or lateral side of the ramus mandibulae.

16. Intraoral distractor according to claim 1, wherein the fixation units, when attached to the ramus and corpus mandibulae, respectively, are displaceable linearly in a direction parallel to a sagittal plane.

17. Intraoral distractor according to claim 16, wherein the joint axis, when the fixation units are attached to the ramus and corpus mandibulae, respectively, is orthogonal to the sagittal plane.

18. Intraoral distractor according to claim 1, wherein the joint is rotated by a segment of a gear with oblique toothing and an engaging worm gear, in order to change a relative angle between ramus mandibulae and corpus mandibulae.

19. Intraoral distractor according to claim 18, wherein the gear segment is attached to the first fixation unit and wherein the worm gear is attached to the second fixation unit.

20. Intraoral distractor according to claim 1, wherein the interfaces between the distraction element and the corresponding fixation unit are each formed by a linear guidance where, when the fixation units are attached to the ramus and corpus mandibulae, respectively, a direction of guidance is substantially parallel to a sagittal plane and substantially orthogonal to an occlusal plane of the mandible.

21. Intraoral distractor according to claim 20, wherein the linear guidance at the interface to the corpus mandibulae is formed by a butt strap reaching into a nut.

22. Intraoral distractor according to claim 20, wherein the linear guidance at the interface at the ramus mandibulae is formed by a tube or a clutch mounted on a rod guidance which is part of the fixation unit.

23. Intraoral distractor according to claim 22, wherein the distraction element can be arranged parallel to the sagittal plane by turning about an axis of the rod guidance.

24. Intraoral distractor according to claim 23, wherein the tube can be moved along the rod guidance in direction of the axis and can be fixated.

\* \* \* \* \*